US00PP09351P

United States Patent [19]

Guillou et al.

[11] Patent Number: Plant 9,351

[45] Date of Patent: Oct. 31, 1995

[54] GERANIUM PLANT NAMED 'GUISHIVA'

[75] Inventors: Jacques Guillou; Bernard Guillou; Maurice Guillou, all of Saint-Malo, France

[73] Assignee: Ets. Guillou Freres, Saint-Malo, France

[21] Appl. No.: 352,713

[22] Filed: Dec. 5, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A distinct cultivar of geranium plant named Guishiva particularly characterized by the combined features of blood red double flowers, deep green foliage with medium zonation, early and rich flowering, medium growth and bushy plant habit.

1 Drawing Sheet

The present invention comprises a new and distinct cultivar of geranium, botanically known as *Pelargonium peltatum l'Hert,* and hereinafter referred to by the cultivar name Guishiva.

Guishiva is a product of a planned breeding program which has the objective of creating new ivy geranium cultivars with intense red flower color, and compact and bushy plant habit.

Guishiva was originated from a hybridization made by the inventors in Saint-Malo, France in 1987. The female and male parents were unnamed hybrids from the proprietary Guillou collection, both parents being characterized by red semi-double flowers.

Guishiva was discovered and selected as one flowering plant within the progeny of the stated cross by the inventors in May 1988 in a controlled environment in Saint-Malo, France.

The first act of asexual reproduction of Guishiva was accomplished in 1989 when vegetative cuttings were taken from the initial selection in 1986 in a controlled environment in Saint-Malo, France, by, or under the supervision of the inventors.

Horticultural examination of plants grown from cuttings initiated in Hillscheid, Federal Republic of Germany, in May 1990 and continuing thereafter has demonstrated that the combination of characteristics as herein disclosed for Guishiva are firmly fixed and are retained through successive generations of asexual reproduction.

Guishiva has not been observed under all possible environmental conditions. The phenotype may vary significantly with variations in environment such as temperature, light intensity and day length, without, however any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Guishiva, which in combination distinguish this geranium as a new and distinct cultivar:

1. Dark red (blood-red) double flowers.
2. Deep green foliage with medium zonation.
3. Medium growth and bushy plant habit.
4. Early flowering.
5. Abundant flowering throughout the year. Of the many known commercial cultivars known to the present inventors, there is no cultivar with which Guishiva can be closely compared.

The accompanying photographic drawing shows typical flower and foliage characteristics of Guishiva, with colors being as true as possible with illustrations of this type.

In the following description color references are made to

The Royal Horticultural Society Colour Chart. Color values were determined indoors in May, from plants grown in greenhouses in Hillscheid, Federal Republic of Germany.

Classification:

*Botanical.*—A hybrid of the species *Pelargonium peltatum l'Hert.*

*Commercial.*—Ivy geraniu, cv. Guishiva.

Inflorescence:

*Umbel.*—Shape — Irregular. Average diameter — 88 mm. Average depth — 43 mm. Peduncle length — 140 mm. Pedicel length — 22 mm. Pedicel color — Green pedicels with "knots" or swellings. Number of flowers per umbel — 12–16.

*Corolla.*—Average diameter — 42 mm. Form — double. Average number of petals — 8–12. Average number of petaloids — 0–2. Color (general tonality from a distance of three meters) — Red. Color of upper petals — 46C. Color of lower petals — 46C. Markings (only on upper petals) — Black veins. Color of lower surfaces of petals — 46C-D. Color of sepals — Green. Number of sepals — 5.

*Bud.*—Shape — Elliptic. Color (adaxial) — Green, no anthocyanine. Color (abaxial) — Red and white, marbled.

*Reproductive organs.*—Androecium — 7 fertile anthers, white filament and orange pollen, black underside. Gynoecium — 5–6 lobed, dark red style and stigma; fruit or seed has not been observed.

*Spring flowering response period.*—In Hillscheid, Federal Republic of Germany in 1993 plants had on average 1.9 flowers opened 15 weeks after planting of unrooted cuttings (pinched plants).

*Outdoor flower production.*—The flower count in 1992 in Hillscheid, Federal Republic of Germany indicated between 85 and 95 flowers per plant for May through August observation period.

*Durability.*—Shatter resistance good.

Plant:

*Foliage.*—Form — Ivy shaped. Margin — Entire. Size of leaf — 75–80 mm. Color of upper surface — Green, approximately 137 B-C. Color of zonation — Brown, approximately 166A. Tolerance of botrytis — Good Surface — Smooth; dull, not reflective.

*General appearance and form.*—*Internode length* — 3–4 cm. Branching pattern — 7.0 branches per plant. Height — 65 cm.

It is claimed:

1. A new and distinct cultivar of geranium plant named Guishiva, as described and illustrated.

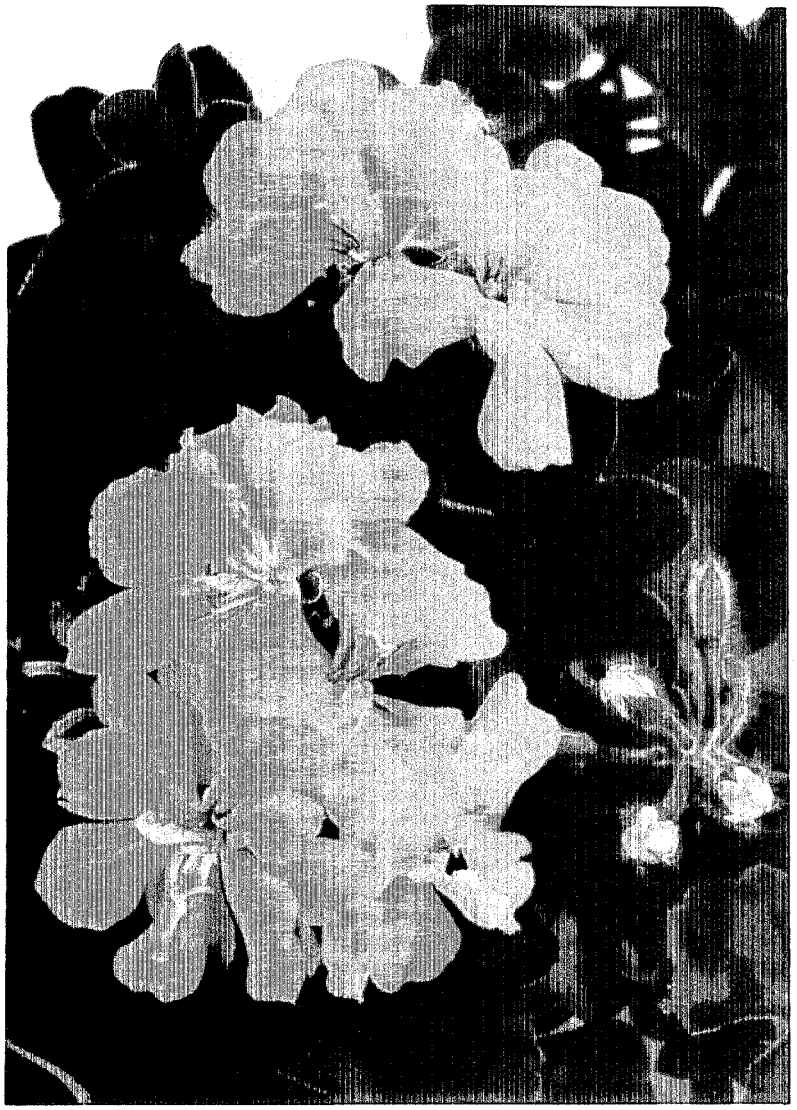

* * * * *